United States Patent

Commons et al.

[11] Patent Number: 5,527,804
[45] Date of Patent: Jun. 18, 1996

[54] 4-CARBAMOYLOXY-PIPERIDINE-1-CARBOXYLIC ACID ESTERS: INHIBITORS OR CHOLESTEROL ABSORPTION

[75] Inventors: Thomas J. Commons, Wayne; Christa M. LaClair, Newtown, both of Pa.

[73] Assignee: American Home Products Corporation, Madison, N.J.

[21] Appl. No.: 259,229

[22] Filed: Jun. 13, 1994

[51] Int. Cl.⁶ .................. A61K 31/445; C07D 221/20; C07D 401/10; C07D 401/12
[52] U.S. Cl. .......... 514/278; 514/255; 514/269; 514/316; 514/317; 514/318; 514/319; 514/320; 514/321; 514/322; 514/323; 514/324; 514/326; 544/298; 544/302; 544/408; 546/16; 546/141; 546/153; 546/188; 546/193; 546/196; 546/198; 546/201; 546/202; 546/205; 546/210; 546/216
[58] Field of Search .................. 546/16, 188, 216, 546/193, 198, 199, 196, 201, 202, 205, 210, 153, 141; 544/298, 302, 408; 514/278, 316, 317, 318, 319, 320, 321, 322, 255, 269, 323, 324, 326, 309, 314

[56] References Cited

U.S. PATENT DOCUMENTS 5,112,859 6/1992 Commons .......................... 514/484
5,169,844 12/1992 Commons .......................... 514/211

FOREIGN PATENT DOCUMENTS 0428385 5/1991 European Pat. Off. ...... C07C 271/40

OTHER PUBLICATIONS

Lombardo "Catalytic properties of modified human pancreatic carboxylic ester hydrolase" Biochim. Biophys. Acra v. 700, 75–80 (1982).
Dipersio et al. "Site specific mutagenesis of an essential histidine residue in pancreatic cholesterol esterase" J. Bio. Chem. v. 266, 4033–4036 (1991).
Britt et al. "Identification of a cocaine esterase in a strain of Psseudomonas maltophilia" J. Bacteriology v. 174, 2087–2094 (1992).

Primary Examiner—Ceila Chang
Attorney, Agent, or Firm—R. F. Boswell, Jr.

[57] ABSTRACT

Compounds which inhibit the enzyme cholesterol ester hydrolase (CEH) thus inhibit the formation of esterified cholesterol. Esterified cholesterol is absorbed through the intestine and inhibition of the enzyme therefore results in inhibition of cholesterol absorption. The compounds of this invention inhibit cholesterol ester hydrolase and have the formula:

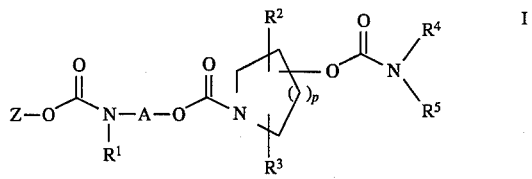

wherein
Z is $-Ar^1$, $-Ar^1-Ar^2$, $-Ar^1-O-Ar^2$, $-Ar^1-S-Ar^2$,

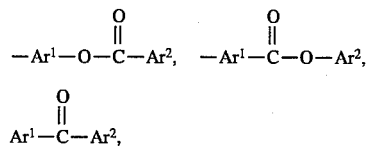

$-Ar^1-(CH_2)_{1-20}-Ar^2$, $-Ar^1-(CH_2)_{1-20}-O-Ar^2$, $-Ar^1-O-(CH_2)_{1-20}-Ar^2$, $-Ar^1-(CR^6=CR^6)_{1-3}-Ar^2$ or $-Ar^1-NR^7-Ar^2$; and A is a hydrocarbon linking group which may be interrupted by a heteroatom or a cycloalkyl, aryl, heterocycloalkyl, or an azacycloalkyl group;

and $R^4$ and $R^5$ are independently alkyl, alkenyl, acyl, alkoxycarbonyl or H or $R^4$ and $R^5$ together with the interposed nitrogen form a saturated heterocyclic ring.

7 Claims, No Drawings

4-CARBAMOYLOXY-PIPERIDINE-1-CARBOXYLIC ACID ESTERS: INHIBITORS OR CHOLESTEROL ABSORPTION

FIELD OF THE INVENTION

The enzymes cholesterol ester hydrolase (CEH) and acyl-CoA cholesterol acyltransferase (ACAT) have been implicated in the reesterification and absorption of exogenous cholesterol. It has been demonstrated that removal of CEH from pancreatic juice results in an 80% reduction in the uptake of cholesterol into the bloodstream in rats [Hoisie, J. Biol. Chem. 262, 260–264 (1987).] The association between high serum cholesterol levels and coronary vascular disease is well documented; consequently compounds of this invention may be useful for treating atherosclerosis, familial hypercholesterolemia, hyperlipidemia, and like diseases.

BACKGROUND OF THE INVENTION

Hosie et al., J. Biological Chem. 252, 260 (1987), discusses the irreversible inhibition of cholesterol esterases by p-nitrophenyl N-alkyl carbamates and the reversible inhibition of cholesterol esterase by cholesterol-N-alkyl carbamates. In our commonly owned U.S. Pat. No. 5,169,844, novel carbamyl esters of 1-[(4-phenoxyphenoxy)carbonyl]-4-piperidinol are disclosed which are cholesterol absorption inhibitors.

SUMMARY OF THE INVENTION

This invention relates to a series of novel compounds which inhibit cholesterol absorption and have the general formula I below

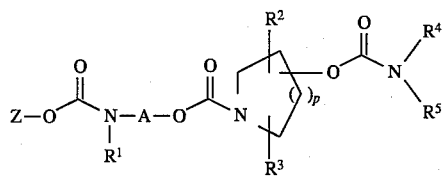

wherein p is 0, 1, 2, 3, or 4;

Z is $-Ar^1$, $-Ar^1-Ar^2$, $-Ar^1-O-Ar^2$, $-Ar^1-S-Ar^2$,

$-Ar^1-(CH_2)_{1-20}-Ar^2$, $-Ar^1-(CH_2)_{1-20}-O-Ar^2$, $-Ar^1-O-(CH_2)_{1-20}-Ar^2$, $-Ar^1-(CR^6=CR^6)_{1-3}-Ar^2$ or $-Ar^1-NR^7-Ar^2$ where $R^6$ is hydrogen or $C_1-C_8$ alkyl and $R^7$ is hydrogen, $C_1-C_8$ alkyl, $C_1-C_8$ alkylcarbonyl or $C_1-C_8$ alkoxycarbonyl;

and $Ar^1$ and $Ar^2$ are independently selected from phenyl, naphthyl, furanyl, benzofuranyl, dibenzofuranyl, pyridinyl, pyrimidinyl, pyrazinyl, thienyl, benzothienyl, imidazolyl, oxazolyl, benzoxazolyl, thiazolyl, benzthiazolyl, isoxazolyl, benzisoxazolyl, indenyl, indolyl, quinolinyl, isoquinolinyl, benzotriazolyl, carbazolyl, benzimidazolyl, or fluorenyl, and $Ar^1$ and $Ar^2$, independently, are optionally substituted by fluorine, chlorine, bromine, iodine, cyano, nitro, $-CO_2H$, $C_1-C_{20}$ alkyl, $C_2-C_{20}$ alkenyl, $C_3-C_8$ cycloalkyl, $C_1-C_{20}$ alkoxy, $C_1-C_{20}$ alkyl$-O-(C_1-C_{20}$ alkyl)$-$, $C_1-C_{20}$ alkyl$-O-(C_1-C_{20}$-alkyl)$-O-$, trifluoromethyl, $C_1-C_{20}$ alkylcarbonyl, $C_3-C_8$ cycloalkyloxy, $C_1-C_{20}$ alkylcarbonyloxy, $C_1-C_{20}$ alkoxycarbonyl, mono or di $C_1-C_{20}$ alkylaminocarbonyl, tetrazolyl, $-OH$, $-(CH_2)_{1-6}-OH$, $-SH$, $-NH_2$ or $-(CH_2)_{1-6}-NR^8R^9$ where $R^8$ is $C_1-C_{20}$ alkyl, $C_1-C_{20}$ alkylcarbonyl, $C_1-C_{20}$ alkoxycarbonyl and $R^9$ is hydrogen or $C_1-C_{20}$ alkyl or $R^8$ and $R^9$ together with the interposed nitrogen atom form a heterocyclic ring of the formula:

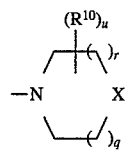

where q is 0, 1 or 2, r is 1 or 2, u is 0, 1 or 2, $R^{10}$ is $C_1-C_8$ alkyl and X is $-O-$, $-S-$, $-NR^{11}-$ where $R^{11}$ is H, $C_1-C_{20}$ alkyl or benzyl or $-CR^{12}R^{13}-$ where $R^{12}$ is H, OH, $C_1-C_{20}$ alkyl, $C_1-C_{20}$ alkoxy, $C_1-C_{20}$ alkylcarbonyloxy, $Ar^1$ or $-(CH_2)_{1-10}-Ar^1$, $R^{13}$ is H, $C_1-C_{20}$ alkyl, or $R^{12}$ and $R^{13}$ together with the interposed carbon forms a 3 to 8 membered carbocyclic ring;

A is a bridging group selected from:

a saturated or unsaturated, straight or branched hydrocarbon chain of 1 to 20 carbons and which may have 1 to 6 sites of olefinic and/or acetylenic unsaturation;

a group of the formula

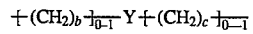

where m and n are 1 to 19, m+n is 2 to 20 and W is a group selected from $-O-$, $-S-$, or $-NR^{14}-$ where $R^{14}$ is hydrogen, $C_1-C_{20}$ alkyl, $C_1-C_{20}$ alkylcarbonyl, $C_1-C_{20}$ alkoxycarbonyl, or benzyl;

a group of the formula:

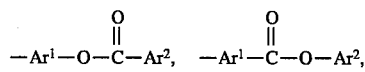

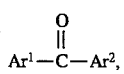

where b and c are 1 to 20, b+c is 1 to 20 and Y is selected from the group consisting of:

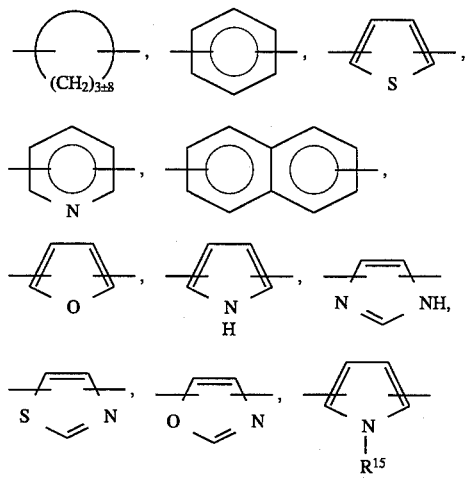

or 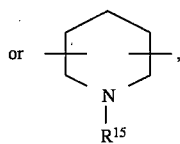

where $R^{15}$ is H, $C_1$–$C_8$ alkyl, $C_1$–$C_{20}$ alkylcarbonyl, $C_1$–$C_{20}$ alkoxycarbonyl, or benzyl; or A together with $R^1$ and the interposed nitrogen form a heterocyclic moiety of the formula:

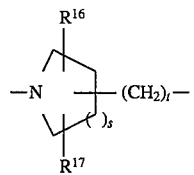

where s is 0, 1, 2, 3 or 4, t is 0 to 15, and $R^{16}$ and $R^{17}$ are, independently, hydrogen, $C_1$–$C_8$ alkyl, $C_1$–$C_8$ alkoxy, $C_1$–$C_8$ alkylcarbonyl, hydroxy, cyano, $C_1$–$C_8$ alkylcarbonyloxy, or —$(CH_2)_{0-6}$—$NR^{18}R^{19}$ where $R^{18}$ is $C_1$–$C_8$ alkyl, $C_1$–$C_8$ alkoxycarbonyl, or $C_1$–$C_8$ alkylcarbonyl and $R^{19}$ is hydrogen or $C_1$–$C_8$ alkyl;

$R^1$ is H, $C_1$–$C_8$ alkyl, phenyl—$(CH_2)_{1-6}$— where phenyl is optionally substituted with a $C_1$–$C_6$ alkyl group, or is combined with A to form a heterocyclic ring as described above;

$R^2$ and $R^3$ are independently $C_1$–$C_8$ alkyl, $C_1$–$C_8$ alkoxy, $C_1$–$C_8$ alkylcarbonyl, hydroxy, cyano, $C_1$–$C_8$ alkylcarbonyloxy, or —$(CH_2)_{0-6}$—$NR^{18}R^{19}$ where $R^{18}$ is $C_1$–$C_8$ alkyl, $C_1$–$C_8$ alkoxycarbonyl, or $C_1$–$C_8$ alkylcarbonyl and $R^{19}$ is hydrogen or $C_1$–$C_8$ alkyl;

$R^4$ and $R^5$ are independently hydrogen, $C_3$–$C_{20}$ alkyl, $C_2$–$C_{20}$ alkenyl, $C_3$–$C_{20}$ cycloalkyl,

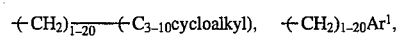

or 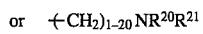

where $R^{20}$ is $C_1$–$C_{20}$ alkyl, $C_2$–$C_{20}$ alkenyl, $C_1$–$C_{20}$ alkylcarbonyl, $C_1$–$C_{20}$ alkoxycarbonyl or benzyl; and $R^{21}$ is hydrogen or $C_1$–$C_{20}$ alkyl, wherein $Ar^1$ is as defined above, or $R^4$ and $R^5$ together with the interposed nitrogen form a heterocyclic moiety of the formula:

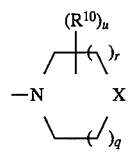

where r, q, u, $R^{10}$ and X are as defined above, or a pharmaceutically acceptable salt thereof.

In the preceding group of compounds, the preferred values for Z are:

Z is —$Ar^1$, —$Ar^1$—$Ar^2$, —$Ar^1$—O—$Ar^2$, —$Ar^1$—S—$Ar^2$,

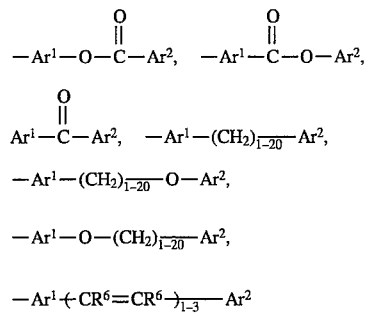

where $R^6$ is H or $C_1$–$C_8$ alkyl, or —$Ar^1$—$NR^7$—$Ar^2$ where $R^7$ is hydrogen, $C_1$–$C_8$ alkyl, $C_1$–$C_8$ alkylcarbonyl or $C_1$–$C_8$ alkoxycarbonyl and $Ar^1$ and $Ar^2$ are selected from phenyl, naphthyl, furanyl, benzofuranyl, dibenzofuranyl, pyridinyl, thienyl, benzothienyl, imidazolyl, oxazolyl, benzoxazolyl, thiazolyl, benzthiazolyl, isoxazolyl, benzisoxazolyl, indenyl, indolyl, quinolinyl, isoquinolinyl, carbazolyl, benzimidazolyl or fluorenyl; and $Ar^1$ and $Ar^2$ may be optionally substituted by fluorine, chlorine, bromine, iodine, cyano, nitro, —$CO_2H$, $C_1$–$C_8$ alkyl, $C_1$–$C_8$ alkoxy, $C_2$–$C_8$ alkenyl, trifluoromethyl, $C_3$–$C_8$ cycloalkyl, $C_3$–$C_8$ cycloalkyloxy, $C_1$–$C_8$ alkylcarbonyl, $C_1$–$C_8$ alkoxycarbonyl, $C_1$–$C_8$ alkylcarbonyloxy, —$NH_2$, —$(CH_2)_{1-6}$—$NR^8R^9$ where $R^8$ is $C_1$–$C_8$ alkyl, $C_1$–$C_8$ alkylcarbonyl or $C_1$–$C_8$ alkoxycarbonyl, and $R^9$ is hydrogen or $C_1$–$C_8$ alkyl.

The preferred values for the bridging group A in the generic description of the compounds of this invention are:

a saturated or unsaturated, straight or branched hydrocarbon chain of 1 to 20 carbon atoms which may have 1 to 6 sites of olefinic and/or acetylenic unsaturation;

a group of the formula:

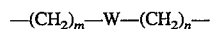

where m and n are 1 to 19, m+n is 2 to 20 and W is a group selected from —O—, —S—, or —$NR^{14}$— where $R^{14}$ is hydrogen, $C_1$–$C_8$ alkyl, $C_1$–$C_8$ alkylcarbonyl, $C_1$–$C_8$ alkoxycarbonyl or benzyl;

a group of the formula

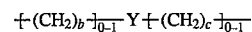

where b and c are 1 to 20, b+c is 1 to 20, and Y is selected from the group consisting of:

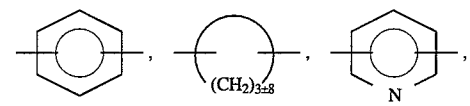

or

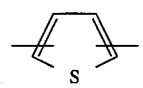

or A together with $R^1$ and the interposed nitrogen form a heterocyclic moiety of the formula:

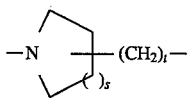

where s is 0, 1, 2 or 3 and t is 0 to 15.

In addition, the preferred values for $R^4$ and $R^5$ are, independently, hydrogen, $C_3$–$C_{20}$ alkyl, $C_2$–$C_8$ alkenyl, $C_3$–$C_8$ cycloalkyl, —$(CH_2)_{1-10}$—($C_3$–$C_{10}$ cycloalkyl), —$(CH_2)_{1-10}Ar^1$, —$(CH_2)_{1-10}$—$NR^{20}R^{21}$ where $R^{20}$ is $C_1$–$C_8$ alkyl, $C_2$–$C_8$ alkenyl, $C_1$–$C_8$ alkylcarbonyl, $C_1$–$C_8$ alkoxycarbonyl or benzyl, and $R^{21}$ is hydrogen or $C_1$–$C_8$ alkyl, or $R^4$ and $R^5$ together with the interposed nitrogen forms a heterocyclic moiety of the formula:

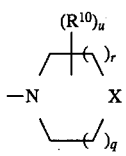

where q is 0, 1 or 2, r is 1 or 2, u is 0, 1 or 2, $R^{10}$ is $C_1$–$C_8$ alkyl and X is —O—, —S—, —$NR^{11}$— where $R^{11}$ is hydrogen, $C_1$–$C_8$ alkyl or benzyl or X is $CR^{12}R^{13}$ where $R^{12}$ is hydrogen, hydroxy, $C_1$–$C_8$ alkyl, $C_1$–$C_8$ alkoxy, and $R^{13}$ is hydrogen or $C_1$–$C_8$ alkyl, or $R^{12}$ and $R^{13}$ together with the interposed carbon forms a 3 to 8 membered carbocyclic ring.

The more preferred compounds according to Formula I are those where:
Z is —$Ar^1$—O—$Ar^2$, $R^1$ is H, $C_1$–$C_8$ alkyl, or phenyl—$(CH_2)_{1-6}$—; A is a $C_1$–$C_{20}$ alkylene group, $R^2$ and $R^3$ are H, p is 2 and $R^4$ is $C_3$–$C_{20}$ alkyl, $C_2$–$C_{20}$ alkenyl, $C_3$–$C_{10}$ cycloalkyl, —$(CH_2)_{1-10}$—$Ar^1$ where $Ar^1$ is phenyl and $R^5$ is H or $R^4$ and $R^5$ together with the interposed nitrogen forms a heterocyclic moiety of the formula:

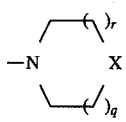

where r and q are 1 and X is $CH_2$ or $CR^{12}R^{13}$ where $R^{12}$ and $R^{13}$ together with the interposed carbon forms a 3–8 membered ring.

The most preferred compounds of Formula I are those where Z is 4-phenoxyphenyl, $R^1$ is H, A is hexyl, p is 2, $R^2$ and $R^3$ are H, $R^4$ is hexyl, decyl, cyclohexyl, or phenylbutyl and $R^5$ is H or $R^4$ and $R^5$ together with the interposed nitrogen forms piperidine or 8-azaspiro[5.4]decane.

In the above description of the novel compounds of this invention, the term "alkyl", used alone or in conjunction with a linking group or functional group such as carbonyl, carbonyloxy, or amino, encompasses branched as well as straight chain hydrocarbons having the number of carbon atoms specified; and the term "alkenyl" includes branched and straight chain alkenes having from 1 to 3 double bonds. The term "alkoxy"; used alone or in conjunction with a linking group or functional group such as carbonyl or carbamoyl, refers to the alkyl—O— moiety where alkyl is as defined above. The term "cycloalkoxy" refers to a —O—cycloalkyl group wherein the cycloalkyl portion of the group has the specified number of carbon atoms. The number and position of substituents on an $Ar^1$ or $Ar^2$ group is governed by the size of the substituent and availability, either commercially or prepared by standard literature procedures and such limitations would be recognized by one skilled in the art of organic synthesis. In general, 1 to 3 substituents would be allowable with the exception of fluorine or chlorine where up to 5 fluorines or chlorines may be present as when the starting material for Z is pentafluorophenol. The term "pharmaceutically acceptable salts" encompasses acid addition salts that may be formed from a basic invention compound and a pharmaceutically acceptable inorganic or organic acid such as hydrochloric, sulfuric, phosphoric, acetic, maleic, fumaric, succinic, citric, tartaric, methanesulfonic acids and the like; a basic salt formed from an acidic invention compound and a pharmaceutically acceptable metal cation such as sodium, potassium, magnesium or calcium, the ammonium salt or an amine salt such as the triethylamine salt, or a quaternary salt formed from a basic invention compound and a pharmaceutically acceptable alkyl or aralkyl halide such as methylbromide or benzylbromide. The compounds of this invention may be recovered in the form of a solvate or hydrate. It is understood that the name of the compound itself encompasses these simple solvates and hydrates.

DETAILED DESCRIPTION OF THE INVENTION

The compounds of this invention may be conveniently prepared by the synthetic reactions shown in Scheme I. For purposes of illustration, the syntheses of the compounds of the specific examples which follow is shown. Other compounds having different selections of the variables Z, $R^1$, A, $R^2$, $R^3$, p, $R^4$ and $R^5$ may be prepared by appropriate substitution of an intermediate or reagent either commercially available or synthesized according to standard literature procedures. Still other methods of preparation of Formula I compounds may be apparent to those skilled in the art.

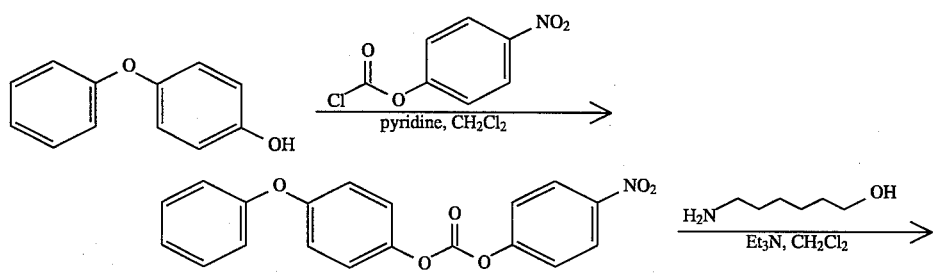

Scheme I

-continued
Scheme I

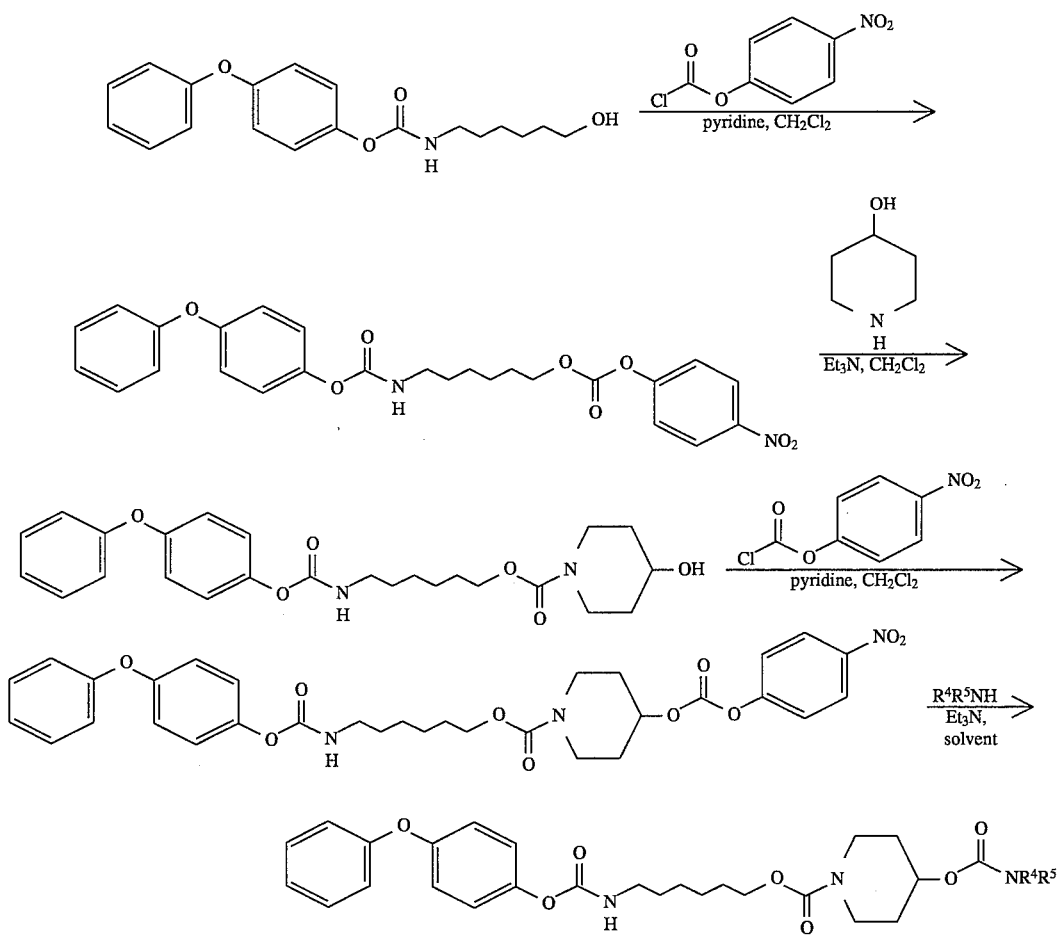

The following specific examples are included for illustrative purposes and are not intended to limit this disclosure in any way.

EXAMPLE 1

Carbonic Acid (4-nitrophenyl)ester (4-phenoxy-phenyl)ester

A solution of 4-phenoxyphenol (50 g, 0.27 mol) and pyridine (22 mL, 0.27 mol) in 500 mL of methylene chloride was added under nitrogen dropwise over 1.5 hours to a solution of 4-nitrophenyl chloroformate (54 g, 0.27 mol) at room temperature. After the addition the reaction was stirred overnight at room temperature. The reaction was extracted two times with 1N HCl, multiple times with saturated $Na_2CO_3$, dried ($MgSO_4$) and the solvent removed under reduced pressure to give 94.86 g of a light yellow crystalline solid. Recrystallization from methylene chloride-diisopropyl ether gave 69.13 g (73%) of the title compound as a light tan crystalline solid, mp 113°–115° C.

Elemental analysis for $C_{19}H_{13}NO_6$ Calc'd: C, 64.96; H, 3.73; N, 3.99 Found: C, 64.63; H, 3.89; N, 3.93

EXAMPLE 2

(6-Hydroxy-hexyl)carbamic acid 4-phenoxy-phenyl ester

A solution of the carbonate prepared in Example 1 (10.0 g, 28.4 mmol) in 75 mL of methylene chloride was added under nitrogen dropwise to a solution of 6-amino-1-hexanol (3.34 g, 28.4 mmol) and triethylamine (19.8 mL, 142 mmol) in 100 mL of methylene chloride at ice-bath temperature. The reaction was stirred at ice bath temperature for approximately eight hours and at room temperature overnight. The reaction was extracted one time with 1N HCl, multiple times with saturated $Na_2CO_3$, dried ($MgSO_4$) and the solvent removed under reduced pressure to give 8.1 g of a solid. Recrystallization of the solid from diisopropyl ether gave 6.55 g (70%) of the title compound as a white crystalline solid, mp 72°–75° C.

Elemental analysis for $C_{19}H_{23}NO_4$ Calc'd: C, 69.28; H, 7.04; N, 4.25 Found: C, 69.20; H, 7.12; N, 4.14

EXAMPLE 3

6-(4-Nitro--phenoxycarbonyloxy)-hexylcarbamic acid 4-phenoxy-phenyl ester

A solution of the alcohol prepared in the previous step (5.67 g, 17.2 mmol) and pyridine (1.39 mL, 17.2 mmol) in 75 mL of methylene chloride was added under nitrogen dropwise to a solution of 4-nitrophenyl chloroformate (3.47 g, 17.2 mmol) in 50 mL of methylene chloride at ice bath temperature. After the addition the cooling bath was removed and the reaction stirred overnight at room temperature. The reaction was extracted one time with 1N HCl, multiple times with saturated $Na_2CO_3$, dried ($MgSO_4$) and the solvent removed under reduced pressure to give 10.01 g of a light yellow crystalline solid. Recrystallization of the solid one time from methylene chloride-diisopropyl ether and two times from methylene chloride gave 5.17 g (61%) of the title compound as an off-white crystalline solid, mp 102°–104° C.

Elemental analysis for $C_{26}H_{26}N_2O_8$ Calc'd: C, 63.15; H, 5.30; N, 5.67 Found: C, 62.80; H, 5.22; N, 5.91

EXAMPLE 4

4-Hydroxy-piperidine-1-carboxylic acid 6-[(4-phenoxy-phenyl)-oxycarbonylamino]-hexyl ester A solution of 4-hydroxypiperidine (2.21 g, 21.8 mmol) and triethylamine (17.5 mL, 91 mmol) in 100 mL of methylene chloride was added under nitrogen dropwise to a solution of the carbonate prepared in Example 3 (9.0 g, 18.2 mmol) in 100 mL of methylene chloride at room temperature. After the addition the reaction was stirred overnight at room temperature. The reaction was extracted one time with 1N HCl, multiple times with saturated $Na_2CO_3$, dried ($MgSO_4$) and the solvent removed under reduced pressure to give 13.16 g of a yellow oil. Purification of the oil on silica gel (230–400 mesh) using hexane-ethyl acetate as the eluent gave 5.87 g (71%) of the title compound as a white waxy solid, mp 48°–55° C.

Elemental analysis for $C_{25}H_{32}N_2O_6$ Calc'd: C, 65.77; H, 7.06; N, 6.13 Found: C, 65.41; H, 7.14; N, 5.98

EXAMPLE 5

4-(4-Nitro-phenoxycarbonyloxy)-piperidine-1-carboxylic acid 6-[(4-phenoxy-phenyl)-oxycarbonylamino]-hexyl ester A solution of the alcohol prepared in Example 4 (5.87 g, 12.9 mmol) and pyridine (1.0 mL, 12.9 mmol) in 50 mL of methylene chloride was added under nitrogen dropwise to a solution of 4-nitrophenyl chloroformate (2.60 g, 12.9 mmol) in 50 mL of methylene chloride at room temperature. The reaction was stirred at room temperature for approximately 48 hours. An additional 2.6 g (12.9 mmol) of 4-nitrophenyl chloroformate was added and the mixture refluxed for approximately 24 hours. The reaction was extracted one time with 1N HCl, multiple times with saturated $Na_2CO_3$, dried ($MgSO_4$) and the solvent removed under reduced pressure to give 6.82 g of a yellow oil. Purification of the oil on silica gel (230–400 mesh) using mixtures of ethyl acetate-methylene chloride as the eluent and then recrystallization from diisopropyl ether of the material isolated gave 1.84 g (22%) of the title compound as a crystalline solid, mp 93°–94° C.

Elemental analysis for $C_{32}H_{35}N_3O_{10}$ Calc'd: C, 61.83; H, 5.68; N, 6.76 Found: C, 62.08; H, 5.60; N, 6.76

EXAMPLE 6

4-(Hexylcarbamoyloxy)-piperidine-1-carboxylic acid 6-[(4-phenoxy-phenyl)-oxycarbonylamino]-hexyl ester A solution of hexylamine (510 μL, 3.86 mmol) and triethylamine (2.24 mL, 16.1 mmol) in 30 mL of methylene chloride was added under nitrogen dropwise to a solution of the carbonate prepared in Example 5 (2.0 g, 3.22 mmol) in 30 mL of methylene chloride at ice bath temperature. After the addition the cooling bath was removed and the reaction stirred at room temperature overnight. An additional 213 μL (1.61 mmol) of hexylamine was added and the reaction stirred at room temperature for 3 hours. The reaction was extracted one time with 1N HCl, multiple times with saturated $Na_2CO_3$, dried ($MgSO_4$) and the solvent removed under reduced pressure to give 1.79 g of a red solid. Recrystallization of the solid from diisopropyl ether gave 1.32 g (70%) of the title compound as a white crystalline solid, mp 84°–86° C.

Elemental analysis for $C_{32}H_{35}N_3O_{10}$ Calc'd: C, 65.84; H, 7.77; N, 7.20 Found: C, 65.93; H, 7.64; N, 7.14

EXAMPLE 7

8-Aza-spiro[4.5]decane-8-carboxylic acid 1-{6-[(4-phenoxy-phenyl)-oxycarbonylamino]-hexyloxycarbonyl}-piperidin-4-yl ester A solution of 8-aza-spiro[4.5]decane hydrochloride (791 mg, 4.50 mmol) and triethylamine (2.24 mL, 16.1 mmol) in 20 mL of anhydrous dimethylformamide was added under nitrogen dropwise to a solution of the carbonate prepared in Example 5 (2.00 g, 3.22 mmol) in 25 mL of anhydrous dimethylformamide. After the addition the reaction was stirred at room temperature overnight. The reaction was diluted with ethyl acetate, extracted one time with 1N HCl, multiple times with saturated $Na_2CO_3$ and then water, dried ($MgSO_4$) and the solvent removed under reduced pressure to give 1.65 g of an oil. Purification of the oil on silica gel (230–400 mesh) using 20% ethyl acetate-methylene chloride as the eluent gave 1.01 g (52%) of the title compound as a light yellow oil, MS [M+H]$^+$622.

Elemental analysis for $C_{35}H_{47}N_3O_7$ Calc'd: C, 67.61; H, 7.62; N, 6.76 Found: C, 66.02; H, 7.44; N, 6.48

EXAMPLE 8

4-(Decylcarbamoyloxy)-piperidine-1-carboxylic acid 6-[(4-phenoxy-phenyl)-oxycarbonylamino]-hexyl ester A solution of decylamine (772 mg, 3.86 mmol) and triethylamine (2.24 mL, 16.1 mmol) in 30 mL of methylene chloride was added under nitrogen dropwise to a solution of the carbonate prepared in Example 5 (2.0 g, 3.22 mmol) in 30 mL of methylene chloride at ice bath temperature. After the addition the cooling bath was removed and the reaction stirred at room temperature for approximately 48 hours. The reaction was extracted one time with 1N HCl, multiple times with saturated $Na_2CO_3$, dried ($MgSO_4$) and the solvent removed under reduced pressure to give 1.90 g of a crystalline solid. Purification of the solid on silica gel (230–400 mesh) using 10%–20% ethyl acetate-methylene chloride as the eluent and recrystallization from diisopropyl ether-methylene chloride of the material isolated gave 672 mg (33%) of the title compound as a white crystalline solid, mp 87°–91° C.

Elemental analysis for $C_{36}H_{53}N_3O_7$ Calc'd: C, 67.58; H, 8.35; N, 6.57 Found: C, 67.30; H, 8.30; N, 6.39

EXAMPLE 9

4-(Cyclohexylcarbamoyloxy)-piperidine-1-carboxylic acid
6-[(4-phenoxy-phenyl)-oxycarbonylamino]-hexyl ester A solution of cyclohexylamine (442 mg, 3.86 mmol) and triethylamine (2.24 mL, 16.1 mmol) in 30 mL of methylene chloride was added under nitrogen dropwise to a solution of the carbonate prepared in Example 5 (2.0 g, 3.22 mmol) in 30 mL of methylene chloride at ice bath temperature. After the addition the cooling bath was removed and the reaction stirred at room temperature for approximately 48 hours. The reaction mixture was extracted one time with 1N HCl, multiple times with saturated $Na_2CO_3$, dried ($MgSO_4$) and the solvent removed under reduced pressure to give 1.92 g of a waxy yellow solid. Purification of the solid on silica gel (230–400 mesh) using 20% ethyl acetate-methylene chloride as the eluent gave 884 mg (47%) of the title compound as a white crystalline solid, mp 138°–142° C.

Elemental analysis for $C_{32}H_{43}N_3O_7$ Calc'd: C, 66.07; H, 7.45; N, 7.22 Found: C, 65.90; H, 7.58; N, 6.99

EXAMPLE 10

4-(4-Phenyl-butyl-carbamoyloxy)-piperidine-1-carboxylic acid
6-[(4-phenoxy-phenyl)-oxycarbonylamino]-hexyl ester A solution of 4-phenylbutylamine (610 µl, 3.86 mmol) and triethylamine (2.24 mL, 16.1 mmol) in 30 mL of methylene chloride was added under nitrogen dropwise to a solution of the carbonate prepared in Example 5 (2.0 g, 3.22 mmol) in 30 mL of methylene chloride at ice bath temperature. After the addition the cooling bath was removed and the reaction stirred at room temperature overnight. An additional 204 µl (1.29 mmol) of 4-phenylbutylamine and 180 µl (1.29 mmol) of triethylamine were added and the reaction stirred at room temperature for approximately 7 hours. The reaction was extracted one time with 1N HCl, multiple times with saturated $Na_2CO_3$, dried ($MgSO_4$) and the solvent removed under reduced pressure to give 2.02 g of a crystalline solid. Purification of the solid on silica gel (230–400 mesh) using 5%–20% ethyl acetate-methylene chloride as the eluent gave 1.43 g (70%) of the title compounds as a white crystalline solid, mp 84°–86° C.

Elemental analysis for $C_{36}H_{45}N_3O_7$ Calc'd: C, 68.44; H, 7.18; N, 6.65 Found: C, 68.53; H, 7.19; N, 6.65

EXAMPLE 11

4-(Piperidine-1-carbonyloxy)-piperidine-1-carboxylic acid
6-[(4-phenoxy-phenyl)oxycarbonylamino]-hexyl ester A solution of piperidine (382 µl, 3.86 mmol) and triethylamine (2.24 mL, 16.1 mmol) in 30 mL of methylene chloride was added under nitrogen dropwise to a solution of the carbonate prepared in Example 5 (2.0 g, 3.22 mmol) in 30 mL of methylene chloride at ice bath temperature. After the addition the cooling bath was removed and the reaction stirred at room temperature overnight. The reaction was extracted one time with 1N HCl, multiple times with saturated $Na_2CO_3$, dried ($MgSO_4$) and the solvent removed under reduced pressure to give 1.85 g of an oil. Purification of the oil on silica gel (230–400 mesh) using 5%–20% ethyl acetate-methylene chloride as the eluent gave 1.23 g (68%) of the title compound as a white crystalline solid, mp 56°–61° C.

Elemental analysis for $C_{31}H_{41}N_3O_7$ Calc'd: C, 65.59; H, 7.28; N, 7.40 Found: C, 65.57; H, 7.28; N, 7.35

Pharmacology

The in vitro and in vivo assays are given below and the biological results are presented in Table I.

In Vitro Assay: The ability of the compounds of this invention to inhibit the formation of cholesteryl esters and thereby interfere with and prevent assimilation of cholesterol into the lymphatic system and ultimately the blood stream was established by incubating the compounds at 37° C. with a mixture of cholesterol and oleic acid in the presence of buffered cholesterol esterase [(EC 3.1.1.13) Sigma Company, St. Louis, Mo., U.S.A., No. C- 1892, from bovine pancreas] and measuring the amount of ester formed, according to the procedure of Field, J. of Lipid Research, 25, 389 (1984).

In Vivo Assay: The in vivo cholesterol absorption studies were conducted in normal rats by oral administration of the compound being tested in propylene glycol and olive oil followed by oral administration of [4-$^{14}$C] cholesterol in propylene glycol and olive oil, otherwise following the procedure of Cayen et al., J. Lipid Res. 20, 162 (1979). The serum radioactivity was measured at six hours after dosing. The results of this study are reported in Table I as percent decrease compared to control.

TABLE I

| Example | In Vitro Results $IC_{50}$ (µM) CEH | In Vivo Results Effect on Absorption of $^{14}$C-Chol-6hr-normal rat % Decrease (mg/kg) |
| --- | --- | --- |
| 6 | 1.1 | 49% (3) |
| 7 | 0.2 ($IC_{25}$) | 50% (10) |
| 8 | 3 | 43% (10) |
| 9 | 0.3 ($IC_{25}$) | 46% (10) |
| 10 | 0.3 ($IC_{25}$) | 61% (10) |
| 11 | 5.9 | 81% (10) |

Thus, the representative compounds of this invention reduce absorption of cholesterol into the blood and thus can be used in the treatment of atherosclerosis, familial hypercholesterolemia, hyperlipidemia and like diseases where a reduction in cholesterol absorption is desired. The dosage requirement for therapeutic use of the antihypercholesterolemic agents of this invention will vary according to the particular compound chosen as well as the age of the patient and severity and nature of the disease being treated. Therapy should be initiated at lower doses, the dosage thereafter being increased, if necessary, to produce the desired effect. In general, the compounds of this invention are most desirably administered at a concentration that will generally afford effective results without causing any harmful or deleterious side effects. Based upon the in vivo potency of the representative anticholesterolemic agents of this invention as reported in the table, the initial dosing will be from about 0.5 to 6 mg/kg with a projected maximum dose of about 100 mg/kg. The preferred dosage range will be from about 1 to 50 mg/kg.

Pharmaceutical Composition

The compounds of formula (I) can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be sufficient at last to impart the desired activity thereto on oral administration. The compounds may also be injected parenterally in which case they are used in the form of a sterile solution containing other solutes, for example, enough saline or glucose to make the solution isotonic.

What is claimed is:

1. A compound having the formula:

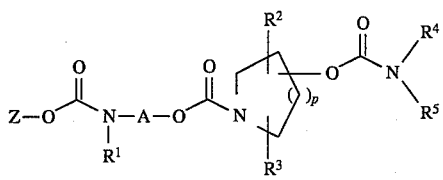

wherein

Z is —Ar$^1$, —Ar$^1$—Ar$^2$, or —Ar$^1$—O—Ar$^2$ wherein Ar$^1$ and Ar$^2$ are independently selected from phenyl, naphthyl, furanyl, benzofuranyl, dibenzofuranyl, pyridinyl, pyrimidinyl, pyrazinyl, thienyl, benzothienyl, imidazolyl, oxazolyl, benzoxazolyl, thiazolyl, benzthiazolyl, isoxazolyl, benzisoxazolyl, indenyl, indolyl, quinolinyl, isoquinolinyl, benzotriazolyl, carbazolyl, benzimidazolyl, or fluorenyl;

R$^1$ is H, C$_1$–C$_8$ alkyl, or phenyl—(CH$_2$)$_{1-6}$—;

A is a C$_1$–C$_{20}$ alkylene group;

R$^2$ and R$^3$ are H;

p is 2 and

R$^4$ and R$^5$ are independently H, C$_3$–C$_{20}$ alkyl, C$_2$–C$_{20}$ alkenyl, C$_3$–C$_{10}$ cycloalkyl, —(CH$_2$—)$_{1-20}$C$_{3-10}$cycloalkyl, —(CH$_2$)$_{1-20}$phenyl, or R$^4$ and R$^5$ together with the interposed nitrogen form a heterocyclic moiety of the formula:

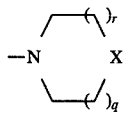

where r and q are 1 and X is CH$_2$ or CR$^{12}$R$^{13}$ where R$^{12}$ and R$^{13}$ together with the interposed carbon from a 3–8 membered carbocyclic ring, or a pharmaceutically acceptable salt thereof.

2. A compound having the formula

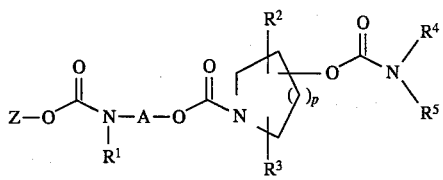

where Z is 4-phenoxyphenyl, R$^1$ is H, A is hexylene, p is 2, R$^2$ and R$^3$ are H, R$^4$ is hexyl, decyl, cyclohexyl, or phenyl-butyl and R$^5$ is H or R$^4$ and R$^5$ together with the interposed nitrogen form piperidine or 8-azaspiro[5.4]decane.

3. A compound selected from:

4-(Hexylcarbamoyloxy)-piperidine-1-carboxylic acid 6-[(4-phenoxy-phenyl)-oxycarbonylamino]-hexyl ester, 8-Aza-spiro[4.5]decane-8-carboxylic acid 1-{6-[(4-phenoxy-phenyl)-oxycarbonylamino]-hexyloxycarbonyl}-piperidin-4-yl ester, 4-(Decylcarbamoyloxy)-piperidine-1-carboxylic acid 6-[(4-phenoxy-phenyl)-oxycarbonylamino]-hexyl ester, 4-(Cyclohexylcarbamoyloxy)-piperidine-1-carboxylic acid 6-[(4-phenoxy-phenyl)-oxycarbonylamino]-hexyl ester, 4-(4-Phenyl-butyl-carbamoyloxy)-piperidine-1-carboxylic acid 6-[(4-phenoxy-phenyl)-oxycarbonylamino]-hexyl ester, or 4-(Piperidine-1-carbonyloxy)-piperidine-1-carboxylic acid 6-[(4-phenoxy-phenyl)oxycarbonylamino]-hexyl ester.

4. A method of reducing cholesterol absorption through the intestinal wall in a mammal which comprises internally administering thereto a therapeutically effective amount of a compound of the formula:

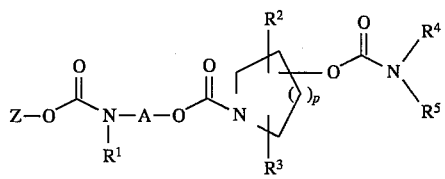

wherein

Z is —Ar$^1$, —Ar$^1$—Ar$^2$, or —Ar$^1$—O—Ar$^2$ wherein Ar$^1$ and Ar$^2$ are independently selected from phenyl, naphthyl, furanyl, benzofuranyl, dibenzofuranyl, pyridinyl, pyrimidinyl, pyrazinyl, thienyl, benzothienyl, imidazolyl, oxazolyl, benzoxazolyl, thiazolyl, benzthiazolyl, isoxazolyl, benzisoxazolyl, indenyl, indolyl, quinolinyl, isoquinolinyl, benzotriazolyl, carbazolyl, benzimidazolyl, or fluorenyl;

R$^1$ is H, C$_1$–C$_8$ alkyl, or phenyl—(CH$_2$)$_{1-6}$—;

A is a C$_1$–C$_{20}$ alkylene group;

R$^2$ and R$^3$ are H;

p is 2 and

R$^4$ and R$^5$ are independently H, C$_3$–C$_{20}$ alkyl, C$_2$–C$_{20}$ alkenyl, C$_3$–C$_{10}$ cycloalkyl, —(CH$_2$—)$_{1-20}$C$_{3-10}$cycloalkyl, —(CH$_2$)$_{1-20}$phenyl, or R$^4$ and R$^5$ together with the interposed nitrogen form a heterocyclic moiety of the formula:

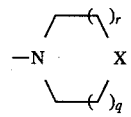

where r and q are 1 and X is CH$_2$ or CR$^{12}$R$^{13}$ where R$^{12}$ and R$^{13}$ together with the interposed carbon form a 3–8 membered carbocyclic ring, or a pharmaceutically acceptable salt thereof.

5. A method of reducing cholesterol absorption through the intestinal wall in a mammal which comprises internally administering thereto a therapeutically effective amount of a compound of the formula:

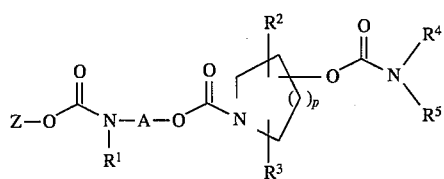

where Z is 4-phenoxyphenyl, $R^1$ is H, A is hexylene, p is 2, $R^2$ and $R^3$ are H, $R^4$ is hexyl, decyl, cyclohexyl, or phenylbutyl and $R^5$ is H or $R^4$ and $R^5$ together with the interposed nitrogen form piperidine or 8-azaspiro[5.4]decane.

6. A method of reducing cholesterol absorption through the intestinal wall in a mammal which comprises internally administering thereto a therapeutically effective amount of a compound selected from:

4-(Hexylcarbamoyloxy)-piperidine-1-carboxylic acid 6-[(4-phenoxy-phenyl)-oxycarbonylamino]-hexyl ester, 8-Aza-spiro[4.5]decane-8-carboxylic acid 1-{6-[(4-phenoxy-phenyl)-oxycarbonylamino]-hexyloxycarbonyl}-piperidin-4-yl ester, 4-(Decylcarbamoyloxy)-piperidine-1-carboxylic acid 6-[(4-phenoxy-phenyl)-oxycarbonylamino]-hexyl ester, 4-(Cyclohexylcarbamoyloxy)-piperidine-1-carboxylic acid 6-[(4-phenoxy-phenyl)-oxycarbonylamino]-hexyl ester, 4-(4-Phenyl-butyl-carbamoyloxy)-piperidine-1-carboxylic acid 6-[(4-phenoxy-phenyl)-oxycarbonylamino]-hexyl ester, or 4-(Piperidine-1-carbonyloxy)-piperidine-1-carboxylic acid 6-[(4-phenoxy-phenyl)oxycarbonylamino]-hexyl ester.

7. A pharmaceutical composition for reducing cholesterol absorption comprising a pharmaceutical carrier and a therapeutically effective amount of a compound of claim 1.

* * * * *